United States Patent [19]

Fay

[11] Patent Number: 4,589,548
[45] Date of Patent: May 20, 1986

[54] SPUTUM COLLECTION APPARATUS

[75] Inventor: John E. Fay, Leominster, Mass.

[73] Assignee: Biomedical Polymers, Inc., Leominster, Mass.

[21] Appl. No.: 679,208

[22] Filed: Dec. 6, 1984

[51] Int. Cl.⁴ .............................................. B65D 83/10
[52] U.S. Cl. ..................... 206/363; 206/569; 215/6; 435/296; 435/299; 435/810
[58] Field of Search ................... 206/363, 569, 570; 215/6; 435/30, 296, 299, 810; 128/760, 763; 4/144.1

[56] References Cited

U.S. PATENT DOCUMENTS

| | | | |
|---|---|---|---|
| 1,657,312 | 1/1928 | McEldowney | 215/6 |
| 2,374,092 | 4/1945 | Glaser | 215/6 |
| 2,509,369 | 5/1950 | Roberson | 220/408 |
| 2,711,766 | 6/1955 | Archer et al. | 215/6 |
| 3,518,164 | 6/1970 | Andelin et al. | 206/459 |
| 3,711,871 | 1/1973 | Sherin | 128/760 |
| 3,923,040 | 12/1975 | Beach | 128/760 |
| 4,062,652 | 12/1977 | Rolfo-Fontana | 435/296 |
| 4,064,760 | 12/1977 | Benjamin | 128/760 |
| 4,116,066 | 9/1978 | Mehl et al. | 128/760 |
| 4,206,842 | 6/1980 | Burridge, Jr. | 220/408 |
| 4,221,295 | 9/1980 | Tuchband et al. | 206/570 |
| 4,283,498 | 8/1981 | Schlesinger | 435/296 |
| 4,335,756 | 6/1982 | Sharp et al. | 206/363 |

*Primary Examiner*—William Price
*Assistant Examiner*—David Fidei
*Attorney, Agent, or Firm*—Joseph S. Iandiorio; William E. Noonan

[57] ABSTRACT

An apparatus for collecting sputum including: a sputum container having an open end and a closed end; and a funnel which includes a mouth at one end and a discharge portion at the other end. The discharge portion is removably attachable to the container to establish fluid communication between the funnel and the container. A cap is provided for removably covering the container opening. Further provided is a base having a top which includes a recess for receiving the closed end of the container to support at least a portion of the container above the base and a chamber with an opening at its lower end. The cap is releasably held within the chamber with the inside of the cap facing the opening.

25 Claims, 4 Drawing Figures

SPUTUM COLLECTION APPARATUS

FIELD OF INVENTION

This invention relates to an apparatus for a safely collecting sputum specimens for testing and diagnosis.

BACKGROUND OF INVENTION

The diagnosis of tuberculosis and other respiratory ailments necessitates the taking of sputum samples for testing and analysis. Such specimens are typically collected by a doctor, nurse or laboratory technician using one of a number of known sputum collection systems.

An important requirement of any sputum collection system is that it minimize the risk of contamination of hospital or lab personnel who handle the device. In an effort to reduce this danger, one device of the prior art employs a graduated cylinder having a funnel attached at one end. A protective outer body encloses the cylinder entirely and attaches to the funnel. The cylinder is mounted within an annular ring on a removable bottom lid of the enclosure. A threaded cap is mounted sideways on the inside wall of the enclosure. After the sputum specimen has been collected the funnel and cylinder are removed from the enclosure and the bottom lid is opened. The open end of the cylinder is inserted into the bottom of the enclosure, and the cylinder is tilted to engage the cap and slide it out of the enclosure and loosely onto the cylinder. The cap is then tightened by hand on the cylinder and centrifuging and testing are performed. The enclosure and funnel are both discarded.

This sputum collection system exhibits a number of disadvantages. For example, it is complex and awkward to use. Because of the sideway position of the cap in the enclosure, it is very difficult to thread the cylinder directly onto the cap while that cap is still in the enclosure. Therefore, the cap must often be slid out of the enclosure and hand-tightened. An extra time-consuming step is thus added and the lab technician's hands are exposed to the risk of inadvertantly contacting the open end of the sputum-containing cylinder. Moreover, sliding the cap out of the receptacle is a very delicate maneuver and it is quite easy for the cap to slip off the cylinder and drop to the floor, where it may be readily contaminated.

The large enclosure presents additional problems. Although the bottom of the enclosure flares slightly, the large longitudinal enclosure still presents a relatively high center of gravity. The device is therefore unstable and tends to tip over when it is transported on a hospital cart, tray or similar apparatus. Furthermore, when the enclosure and funnel are removed the annular ring in the bottom lid is insufficient to independently hold the cylinder upright. The enclosure and funnel are themselves discarded, and in any event it is unsanitary, awkward and wholly impractical to reassemble the enclosure to enable the capped cylinder to stand upright. Therefore, a separate rack is required for storing or transporting the specimen-containing cylinder. Additionally, the size of the enclosure adds to the complexity and costs of manufacturing the device.

SUMMARY OF INVENTION

It is therefore an object of this invention to provide an improved sputum collection apparatus which after a specimen has been taken may be conveniently disassembled and which permits the operator to quickly, easily and safely cap the sputum specimen container without touching either the cap or the open end of the container.

It is a further object of this invention to provide a sputum collection apparatus which may be effectively sealed to prevent contamination of laboratory and hospital personnel.

It is a further object of this invention to provide a sputum collection apparatus which is simply and efficiently constructed and relatively inexpensive to manufacture.

It is a further object of this invention to provide a sputum collection apparatus which provides stable support for a capped specimen container during transportation and storage without the need for a separate laboratory rack.

It is a further object of this invention to provide a sputum collection apparatus which is aesthetically pleasing and transparent to permit improved observation and testing.

This invention features an apparatus for collecting sputum which includes a sputum container having an open end and a closed end. There is a funnel which includes a mouth at one end and a discharge portion at the other end. The discharge portion is removably attachable to the container to establish fluid communication between the funnel and the container. A cap is provided for removably covering the container opening. A base is provided having a top which includes a recess for receiving the closed end of the container to support at least a portion of the container above the base. The base also includes a chamber with an opening at its lower end, and means are mounted within the chamber for releasably holding the cap with the inner end of the cap facing the opening.

In a preferred embodiment the container is elongate and includes a tube having graduated indicia thereon. The tube may include thread means proximate the open end thereof, and the cap may include complementary thread means for engaging the thread means of the tube to cover the tube with the cap.

An upper lid may be provided for selectively closing the mouth of the funnel. The upper lid may include ridge means disposed on the inside surface thereof and receivable within the mouth of the funnel for sealably engaging the inner surface of the funnel. Hinge means may interconnect the upper lid and the funnel, and the funnel, hinge means and upper lid may be integrally formed. A lower lid may be provided for selectively closing the lower end of the base. Hinge means may interconnect the lower lid and the base. The base, hinge means and lower lid may be interconnected. The lower lid may include a substantially flat periphery which in the lid closed condition extends outwardly beyond the edge of said base.

The discharge portion may include an inner lip receivable within the opening of the container for sealably engaging the inner wall of the container, and an outer peripheral lip arranged coaxially with the inner lip for receiving the open end of the container and sealably engaging the outside surface of the container.

The recess may include a lower generally conical section and an upper generally cylindrical section for receiving mating conical and cylindrical sections of the container. The means for holding typically includes means for gripping the periphery of the cap. Such means for gripping preferably includes a plurality of radial projections spaced about a chamber and extending inwardly from the wall of the chamber to engage the periphery of the cap and provide a friction fit between the cap and the projections. Three such radial projections may be employed. Each projection may include a first surface for engaging the peripheral surface of the cap and a second surface for engaging the top surface of the cap. Typically the means for holding locates the cap centrally within the base. The cap may be translucent or opaque.

DISCLOSURE OF PREFERRED EMBOIDMENT

Other objects, features and advantages will occur from the following description of a preferred embodiment and the accompanying drawings, in which:

FIG. 4 is an elevational view of a capped sputum container reinserted within the base for transportation or storage.

Figure 1:
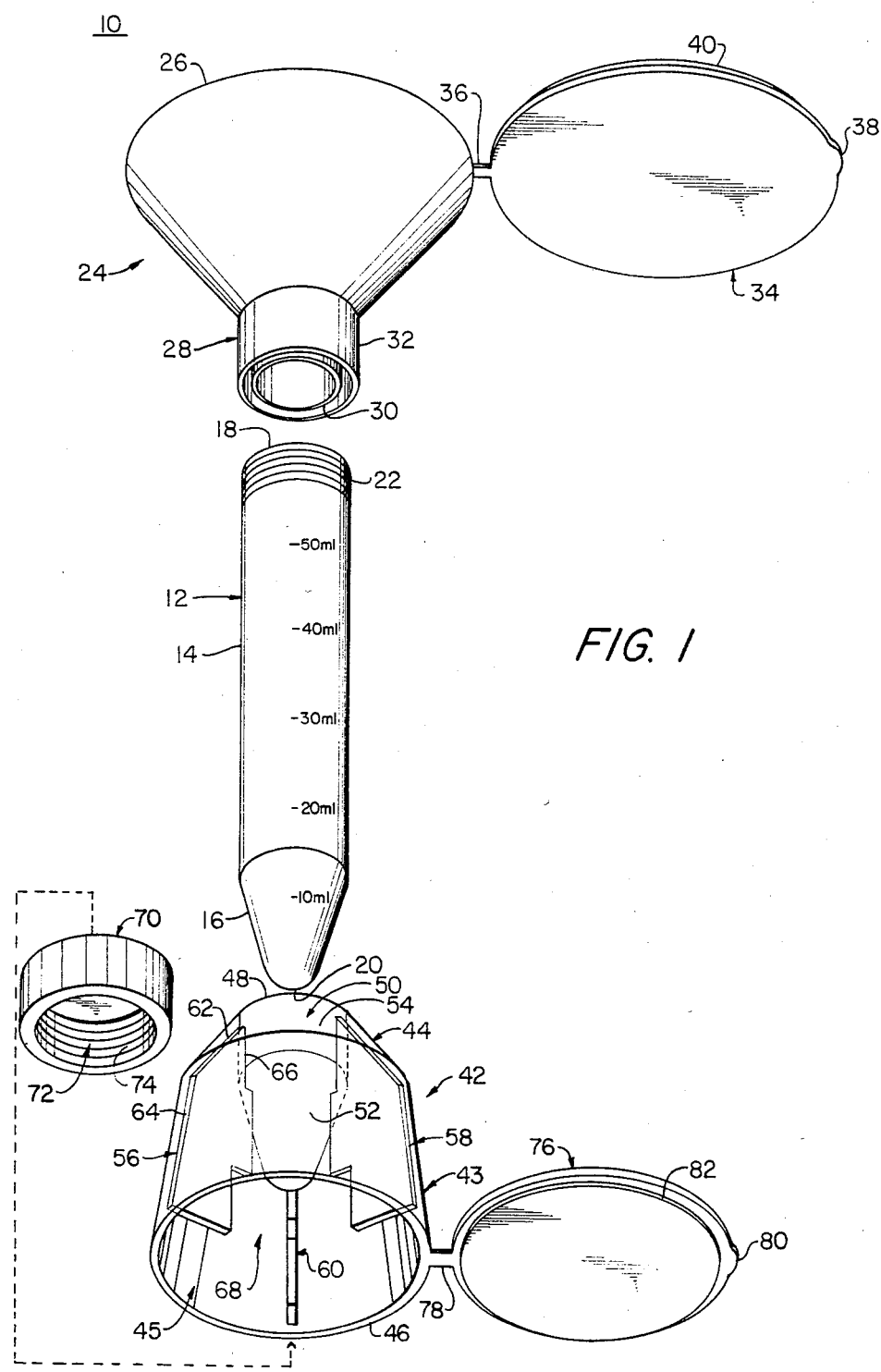
FIG. 1 is an exploded view of the sputum collection apparatus of this invention.

A sputum collection apparatus according to this invention may be effected using a typically elongate tubular container which serves to hold the collected sputum specimen. The container is typically a graduated (e.g. 50 ml) test tube which may be conveniently employed for centrifuging and other lab tests. The tube is typically translucent to permit enhanced observation. It preferably includes a conical, closed lower end and an open cylindrical upper end having peripheral threads to permit attachment of a threaded cap. The cap may be transparent or opaque.

A funnel which includes a mouth at one end and a discharge portion at the other end is also provided. The discharge portion is removably attachable to the container to establish fluid communication between the funnel and the container. The discharge portion of the funnel typically includes an inner annular lip which is receivable within the opening of the tubular container and which sealably engages the inner wall of that container. The discharge portion also includes an outer peripheral lip which is arranged coaxially with the inner lip and which itself receives the open end of the container and sealably engages with the outside surface thereof. An upper lid is attached, typically integrally by means such as a "living" hinge attached to the funnel. The lid selectively opens and closes the mouth of the funnel. It preferably includes ridge means on the inside surface thereof which are receivable within the mouth of the funnel and which sealably engage the inner surface of the funnel.

The ridge means provided on the inside surface of the upper lid provides a very effective seal for the mouth of the funnel. Likewise, the inner and outer annular lips of the discharge portion of the funnel provide an improved and very effective seal with the upper open end of the specimen tube. Whereas funnels of the prior art engage only the inside surface of the specimen receptacle, the instant discharge portion provides sealing engagement with both the inner and outer surfaces of the specimen tube. Sealing is enhanced and the risk of contamination is thereby lessened.

The tubular container and attached funnel are supported by a base having a top which includes a recess for receiving the closed end of the container. At least a portion of the container extends above the base. The recess preferably includes a lower, generally conical section for receiving the mating conical closed end of the container, and an upper, generally cylindrical section for receiving the mating cylindrical section of the container. The base includes a chamber having an opening at its lower level. Means are mounted within the chamber for releasably holding the cap, with the inside of the cap facing the opening. It is preferred that such means for holding include means for gripping the periphery of the cap. The means for gripping may be a plurality of radial projections spaced about the chamber and extending inwardly from the wall thereof to provide a friction fit between the cap and the projection. Typically three such projections are provided, although more or less than three projections are certainly within the scope of this invention. Each such projection may include a first surface for engaging the peripheral surface of the cap and a second surface for engaging the top surface of the cap. The means for holding typically locates the cap centrally within the base. Such a construction is clearly advantageous over devices prior art. It enables the container, filled with a sputum specimen, to be threaded conveniently and directly, without hindrance, into the cap within the chamber. The tube need not be tilted and there is no need to delicately slide the cap out of a slot or to manually touch or tighten the cap in any manner. Furthermore, the risk of inadvertantly dropping the cap is reduced.

It is preferred that a lower lid be provided for selectively closing the chamber opening. The lower lid, like the upper lid, is typically integrally attached to the base by means such as a "living" hinge. The lower lid also includes ridge means on its inner surface which are receivable in the chamber opening of the base and which sealably engage the inside surface of the base. The lower lid preferably has a substantially flat periphery etending outwardly beyond the edge of the base. The lower lid is typically closed during collection of the sputum specimen and then opened to permit attachment of the container to the cap mounted within the base chamber.

The base provides for enhanced stability for the sputum collection apparatus. The base exhibits a much lower center of gravity than is provided by the full-length enclosures of previous devices. The lower lid, which may include inner ridge means receivable within the chamber, and a substantially flat periphery extending outwardly beyond the edge of the base, further enhances the stability of the device. The apparatus is less likely to tip over as it is being transported on hospital or lab trays or carts. The construction of the base also permits it to be conveniently used as a storage or transporting holder for a capped specimen container. Following collection of the sputum, the capped specimen container is quickly and simply replaced within the base without the need for reattaching an enclosure. The discarded contaminated funnel is likewise no longer required. The specimen-containing tube may then be transported on a hospital tray, or stored, for example in a refrigerator, without the necessity of a separate test tube rack.

For simplicity of manufacture, the container and cap, as well as the funnel and base and the lids attached thereto, may also be composed of a transparent material such as plastic. The molding and manufacture of the apparatus is thus greatly simplified.

Because the base is designed to hold only the bottom end of the tube, unlike the larger enclosures of the prior art, the present invention reduces the materials needed for construction and thereby reduces the cost of manufacturing the device.

There is shown in FIG. 1 a sputum collection device 10 which includes a translucent 50 ml tubular container 12 having a cylindrical portion 14 and a conical portion 16. Cylindrical portion 14 includes an open end 18 and conical portion 16 terminates in a closed lower end 20. Threads 22 are disposed circumferentially about cylindrical portion 14 proximate open end 18.

Funnel 24 includes a large mouth 26 at one end and a discharge portion 28 at the other end. Discharge portion 28 includes an inner annular lip 30 which is receivable within open end 18 of container 12 and a peripheral lip 32 which is arranged coaxially with lip 30 and which receives open end 18 of container 12. An upper lid 34 is integrally attached by a hinge 36 to funnel 24. Lid 34 includes a tab 38 for grasping the lid and circular ridge means 40 spaced from the edge of the lid.

Base 42 includes a lower section 43 which has a slight converging taper from bottom to top and an upper section 44 which exhibits a much greater converging taper from bottom to top. Base 42 encloses a chamber 45 which has a circular opening 46 at the lower end thereof. The top 48 of base 42 includes a recess 50 which extends into chamber 45. Recess 50 includes a lower conical section 52 for receiving mating conical portion 16 of container 12. Recess 50 also includes an upper cylindrical section 54 for receiving mating cylindrical section 14 of container 12.

Three projection elements 56, 58 and 60 are mounted within chamber 45. For example, as illustrated by element 56, each projection element includes an edge 62 which engages upper section 44 of base 42, an edge 64 which engages lower section 43 of base 42, and an edge 66 which engages the upper cylindrical section 54 of recess 50. The projection element may be secured within the chamber by applying glue or epoxy between any of these respective lines of engagement. Alternatively the projection elements may be made integral with the base. The projection elements 56, 58 and 60 extend radially inwardly from the walls of chamber 45 and define a space 68 within which cap 70 may be accommodated so that the inside 72 of cap 70 faces opening 46 of chamber 45. The inside periphery of cap 70 includes threads 74.

A lower lid 76, similar to upper lid 34, is integrally attached to base 42 by a hinge 78. Lid 76 includes a peripherally disposed tab 80 for enabling convenient opening and closing of the lid and ridge means 82 on the inside surface thereof.

Figure 2:
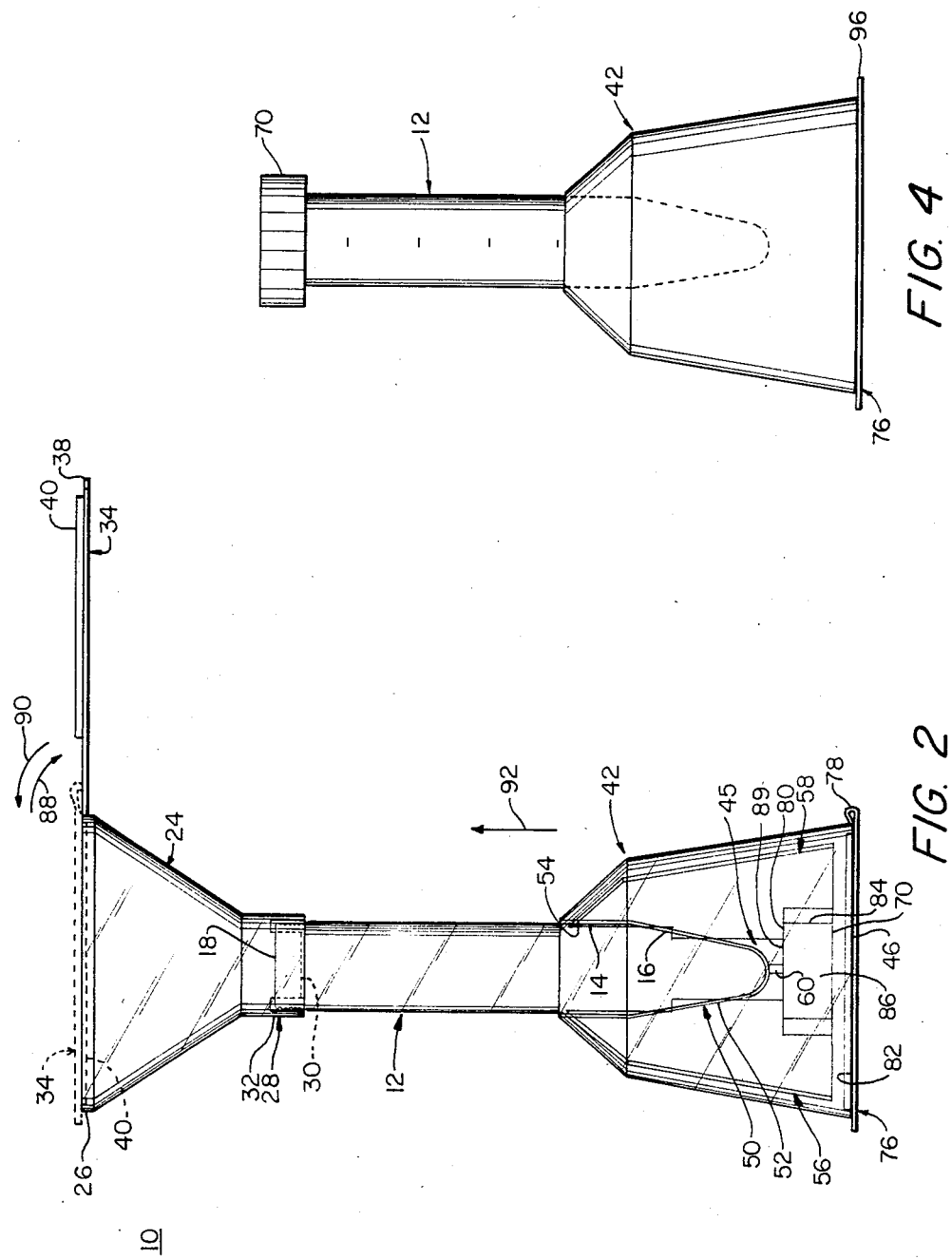
FIG. 2 is an elevational view of the sputum collection apparatus of FIG. 1 illustrating the opening and closing of the upper lid thereof.

As shown in FIG. 2, when funnel 24 is attached to container 12, the inside annular lip 30 of discharge portion 28 is received within the open end 18 of container 12 and sealably engages the inside surface of the tubular container. Container 12 is itself received within peripheral lip 32 of discharge portion 28 which sealably engages the outer surface of the container, and specifically the threads 22 thereof. Such inner and outer sealing of the open end 18 of container 12 insures against accidental specimen leakage and/or contamination of the operator or outside of the container.

Container 12 is inserted into recess 50 of base 42 so that conical container section 16 mates with conical recess section 52 and cylindrical container section 14 mates with cylindrical recess section 54. The remainder of cylindrical section 14 of container 12 extends above base 42.

Cap 70 is disposed centrally within chamber 45 and is peripherally gripped therein so that the inside of the cap faces the opening of base 12. Specifically, cap 70 fits within the space defined by elements 56, 58 and 60. Each element, for example element 58, includes a surface 84 which engages the periphery 86 of cap 70 and a surface 80 which engages the top surface 89 of cap 70. The tolerance is such that cap 70 is held in a friction fit with the elements 56, 58 and 60.

During collection of the sputum specimen, lid 76 is closed so that hinge 78 bends and ridge means 82 are received within chamber opening 46 so that the ridge means sealably engage the inside wall of chamber 45.

To collect a specimen, tab 38 is grasped and upper lid 34 is opened in the direction of arrow 88. The patient then deposits the sputum sample into the funnel 24 so that it is conducted into container 12. Lid 34 is closed in the direction of arrow 90 so that ridge means 40 are received by funnel mouth 26 and sealably engage the inside surface of the funnel 24 proximate mouth 26.

Figure 3:
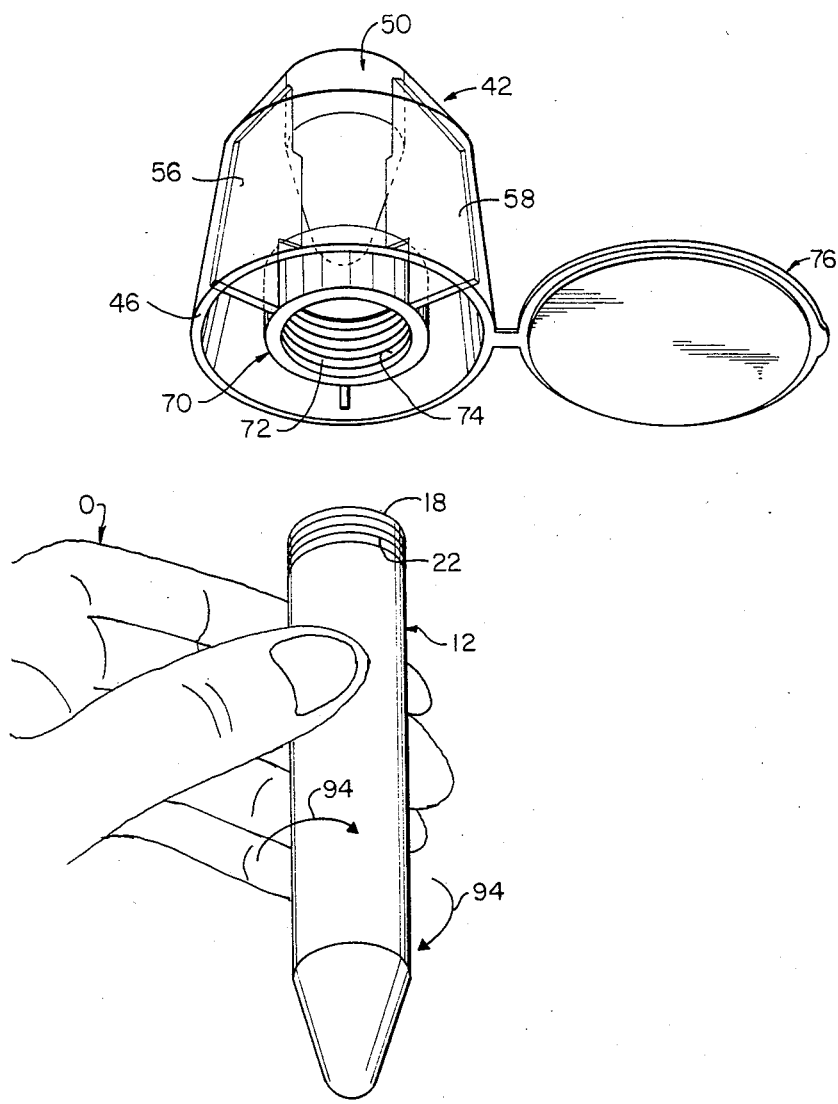
FIG. 3 is an axonometric view illustrating the manner in which the tubular sputum container is threadably attached to the cap located within the base of the device.

When collection of the specimen has been completed, the funnel is removed from container 12 and discarded. Container 12 is then lifted from base 42 in the direction of arrow 92. As shown in FIG. 3, lower lid 76 is opened, thereby exposing the inside of cap 70. Operator O grasps container 12, inserts open end 18 of the container through base opening 46, and simply engages the open end 18 of container 12 with the inside 72 of centrally located cap 70. Container 12 is rotated in the direction of arrows 94 to engage the threads 22 of container 12 with threads 74 of cap 70. The cap is thereby secured to the container. The capped container is then simply and safely pulled out of base 42.

Although the capped container 12 may then be accommodated by a test tube rack or similar device until it is needed for centrifuging or other testing, base 42 may also be used as such a holder. As shown in FIG. 4, capped container 12 is simply reinserted in the recess within base 42. Lower lid 76 is reclosed, and the capped container and base may be placed on a hospital cart for transport or in a refrigerator or other storage area. The relatively low center of gravity of base 42 enables the device to resist tipping. The flat peripheral edge 96 of lower lid 76 also contributes to the stability of the base. Need for a separate test tube rack is thus eliminated.

Other embodiments will occur to those skilled in the art and are within the following claims:

What is claimed is:

1. An apparatus for collecting sputum comprising:
   a sputum container having an open end and a closed end;
   a funnel including a mouth at one end and a discharge portion at the other end, said discharge portion being removably attachable to said container to establish fluid communication between said funnel and said container;
   a cap for removably covering the container opening; and
   a short base remote from said funnel and having a top which includes a recess for receiving the closed end of said container to support at least a portion of said container above said base, said container being the sole structural interconnection between said funnel and base, said base includes a chamber with an opening at its lower end, and means mounted within said chamber for releasably holding said cap with the inside of said cap facing said chamber opening to enable said cap to be attached to said container and cover the open end of said container when said container is introduced generally axially into said base and be properly seated on and removed by said container without direct handling when said container is withdrawn from said base.

2. The apparatus of claim 1 in which said container is elongate.

3. The apparatus of claim 1 in which said container is a tube.

4. The apparatus of claim 3 in which said tube includes graduated indicia thereon.

5. The apparatus of claim 3 in which said tube includes thread means proximate the open end thereof and said cap includes complementary thread means for engaging the thread means of said tube to cover said tube.

6. The apparatus of claim 1 further including an upper lid for selectively closing the mouth of said funnel.

7. The apparatus of claim 6 in which hinge means interconnect said upper lid and said funnel.

8. The apparatus of claim 7 in which said funnel, hinge means and upper lid are integrally interconnected.

9. The apparatus of claim 1 further including a lower lid for selectively closing the open lower end of said base.

10. The apparatus of claim 9 in which hinge means interconnect with said lower lid and said base.

11. The apparatus of claim 10 in which said base, hinge means and lower lid are integrally interconnected.

12. The apparatus of claim 6 in which said upper lid includes ridge means disposed on the inside surface thereof and receivable within the mouth of said funnel for sealably engaging with the inner surface of said funnel.

13. The apparatus of claim 9 in which said lower lid includes ridge means disposed on the inside surface thereof and receivable within the opening of said base for sealably engaging with the inner surface of said funnel.

14. The apparatus of claim 1 in which said discharge portion includes an inner annular lip receivable within the opening of said container for sealably engaging the inner wall of said container and an outer peripheral lip arranged coaxially with said inner lip for receiving the open end of said container and sealably engaging the outside surface of said container.

15. The apparatus of claim 1 in which said recess includes a lower generally conical section and an upper generally cylindrical section for receiving mating conical and cylindrical sections of said container.

16. The apparatus of claim 1 in which said means for holding includes means for gripping the periphery of said cap.

17. The apparatus of claim 16 in which said means for gripping includes a plurality of radial projections spaced about said chamber and extending inwardly from the wall of said chamber to provide a friction fit between the periphery of said cap and said projections.

18. The apparatus of claim 1 in which said means for holding locates said cap centrally within said base.

19. The apparatus of claim 17 in which said means for holding includes three radial projections.

20. The apparatus of claim 17 in which each projection includes a first surface for engaging the peripheral surface of said cap and a second surface for engaging the top surface of said cap.

21. The apparatus of claim 9 in which said lower lid includes a substantially flat periphery which in the lid closed condition extends outwardly beyond the edge of said base.

22. The apparatus of claim 1 in which said cap is translucent.

23. The apparatus of claim 1 in which said cap is opaque.

24. An apparatus for collecting sputum comprising:
a tubular sputum container having an open end and a closed end;
a funnel including a mouth at one end and a discharge portion at the other end, said discharge portion being removably attachable to said container to establish fluid communication between said funnel and said container;
a cap for removably covering the container opening; and
a short base remote from said funnel and having a top which includes a recess for receiving the closed end of said container to support at least a portion of said container above said base, said container being the sole structural interconnection between said funnel and base, said base including a chamber with an opening at its lower end, and means mounted within said chamber for releasably gripping the periphery of said cap with the inside of said cap facing said chamber opening to enable said cap to engage and cover the open end of the container when said container is introduced generally axially into said base and be properly seated on and removed by said container without direct handling when said container is withdrawn from said base.

25. An apparatus for collecting sputum comprising:
a tubular sputum container having an open end and a closed end;
a funnel including a mouth at one end and discharge portion at the other end, said discharge portion being removably attachable to said container to establish fluid communication between said funnel and said container;
a cap for removably covering the container opening; and
a short base remote from said funnel and having a top which includes a recess for receiving the closed end of said container to support at least a portion of said container above said base, said container being the sole structural interconnection between said funnel and base, said base including a chamber with an opening at its lower end, and means mounted within said chamber for releasably gripping the periphery of said cap including a plurality of radial projections spaced about said chamber and extending inwardly from the wall of said chamber to grip the periphery of said cap with the inside of said cap facing said chamber opening to enable said cap to engage and cover the open end of the container when said container is introduced generally axially into said base and be properly seated on and removed by said container without direct handling when said container is withdrawn from said base.

* * * * *